US008993302B2

(12) United States Patent
Conlan et al.

(10) Patent No.: US 8,993,302 B2
(45) Date of Patent: Mar. 31, 2015

(54) **MUTANTS OF *FRANCISELLA TULARENSIS* AND USES THEREOF**

(75) Inventors: Joseph Wayne Conlan, Ottawa (CA); Anders Sjostedt, Umea (SE)

(73) Assignee: National Research Council of Canada, Ottawa, ON. (CA)

(*) Notice: Subject to any disclaimer, the term of this patent is extended or adjusted under 35 U.S.C. 154(b) by 213 days.

(21) Appl. No.: 13/266,466

(22) PCT Filed: Apr. 23, 2010

(86) PCT No.: PCT/CA2010/000637
§ 371 (c)(1),
(2), (4) Date: Oct. 27, 2011

(87) PCT Pub. No.: WO2010/124377
PCT Pub. Date: Nov. 4, 2010

(65) Prior Publication Data
US 2012/0082698 A1    Apr. 5, 2012

Related U.S. Application Data

(60) Provisional application No. 61/213,030, filed on Apr. 29, 2009.

(51) Int. Cl.
*C12N 1/20* (2006.01)
*A61K 39/02* (2006.01)
*C12N 9/90* (2006.01)
*C12N 9/10* (2006.01)

(52) U.S. Cl.
CPC . *C12N 9/90* (2013.01); *C12N 9/104* (2013.01)
USPC .................. 435/252.1; 424/184.1; 424/190.1; 424/234.1

(58) Field of Classification Search
CPC ..................... A61K 2039/522; A61K 39/0208; A61K 38/00; A61K 39/07; A61K 39/085; A61K 2035/122; A61K 2039/523; A61K 39/002; A61K 39/015; C12N 1/36; C12N 15/52; C12N 15/74; C12N 9/90; C12N 9/93; C07K 14/31; C07K 14/32; C07K 16/127
USPC .......... 424/139.1, 141.1, 165.1, 184.1, 234.1, 424/185.1, 190.1, 192.1, 200.1, 243.1, 424/244.1, 273.1, 93.2, 93.4; 435/70.2, 435/70.21, 252.1, 252.3, 41, 6.1, 6.11; 530/387.1
See application file for complete search history.

(56) References Cited

FOREIGN PATENT DOCUMENTS

| CA | 2606673 | 10/2006 |
|----|---------|---------|
| WO | 2010/124377 | 11/2010 |

OTHER PUBLICATIONS

Meibom et al 2008 Molecular Microbiology 67(6) pp. 1384-1401.*

Su Jingliang et al, Genome-wide identification of *Francisella tularensis* virulence determinants, Infection and Immunity, American Society for Macrobiology, vol. 75, No. 6, 2007, pp. 3089-3101.
Hornick et al., Aerogenic immunization of man with live Tularemia vaccine, Microbiol. Mol. Biol. Rev., vol. 30, No. 3, 1966, pp. 532-538.
Extended European Search Report issued on Nov. 27, 2012 for corresponding EP Appln No. 10769182.6.
Examiner's Report issued Feb. 10, 2014 for corresponding EP Appln No. 10769182.6.
European Patent Office Communication dated Dec. 15, 2011 for EP10769182.6.
Written Opinion and International Search Report dated Jul. 5, 2010 for PCT/CA2010/000637.
International Preliminary Examination Report dated Nov. 1, 2011 for PCT/CA2010/000637.
Anthony LSD, Kongshavn PAL. Experimental murine tularemia caused by *Francisella tularensis* live vaccine strain:a model of acquired cellular resistance. Microb Pathog 1987; 2: 3-14.
Chen W, Shen H, Webb A, KuoLee R, Conlan JW. Tularemia in BALB/c and C57BL/6 mice vaccinated with *Francisella tularensis* LVS and challenged intradermally, or by aerosol with virulent isolates of the pathogen; protection varies depending on pathogen virulence, route of exposure, and host genetic background. Vaccine 2003; 21: 3690-700.
Conlan JW, Shen H, Webb AC, Perry MB. Mice vaccinated with the O-antigen of *Francisella tularensis* LVS lipopolysaccharide conjugated to bovine serum albumin develop varying degrees of protective immunity against systemic or aerosol challenge with virulent type A and type B strains of the pathogen. Vaccine 2002; 20: 3465-3471.
Conlan, J.W., Shen, H., KuoLee, R., Zhao, X., Chen, W. Aerosol-, but not intradermal- immunization with the live vaccine strain of *Francisella tularensis* protects mice against subsequent aerosol challenge with a highly virulent type A strain of the pathogen by an áâ T cell- and interferon gamma- dependent mechanism. Vaccine 2005; 23: 2477-85.
Conlan J W, Shen H Golovliov I, Zingmark C, Oyston PCF, Chen W, et al.. Differential ability of novel attenuated targeted deletion mutants of Francisella tularensis subspecies tularensis strain SCHU S4 to protect mice against aerosol challenge with virulent bacteria: effects of host background and route of immunization. Vaccine 2010; 28: 1824-31.
Forslund A-L, Kuoppa K, Svennson K, Salomonsson E, Johansson A, Bystrom M et al. Direct repeat-mediated deletion of a type IV pilin gene results in major virulence attenuation of *Francisella tularensis*. Mol. Microbiol. 2006; 59: 1818-1830.
Fulop M, Mastroeni P, Green M, Titball RW. Role of antibody to lipopolysaccharide in protection against low- and high- virulence strains of *Francisella tularensis*. Vaccine 2001; 19: 4465-72.

(Continued)

*Primary Examiner* — Padma V Baskar
(74) *Attorney, Agent, or Firm* — Catherine Lemay

(57) ABSTRACT

The present invention relates to a mutant *Francisella tularensis* strain comprising an inactivated clpB gene and compositions comprising such mutant. Methods of producing the mutant are also described. The present invention also encompasses a method of conferring immunity against *F. tularensis* in a host, comprising administering the described mutant *F. tularensis* strain.

10 Claims, 6 Drawing Sheets

(56) References Cited

OTHER PUBLICATIONS

Golovliov I, Sjostedt A, Mokrievich A, V. Pavlov V. A method for allelic replacement in *Francisella tularensis*. FEMS Microbiol Lett 2002; 222:273-80.

Green M, Choules G, Rogers D, Titball RW. Efficacy of the live attenuated *Francisella tularensis* vaccine (LVS) in a murine model of disease. Vaccine 2005; 23: 2680-86.

Kadzhaev K, Zingmark C, Golovliov I, Bolanowsi M, Shen H, Conlan W, et al. (2009). Identification of genes contributing to the virulence of *Francisella tularensis* SCHU S4 in a mouse intradermal infection model. PLoS One 2009; 4(5): e5463.

Kuolee R, Harris G, Conlan JW, Chen W. Oral immunization of mice with the live vaccine strain (LVS) of *Francisella tularensis* protects mice against respiratory challenge with virulent type A *F. tularensis*. Vaccine 2007; 25: 3781-91.

Lindgren H, Shen H, Zingmark C, Golovliov I, Conlan W, Sjostedt A. The resistance of *Francisella strains* against reactive nitrogen and oxygen species with special reference to the role of KatG. Infect. Immun 2007; 75: 1303-1309.

Meibom KL. Dubial I, Dupuis M, Barel M, Lenco J, Stulik J et al. The heat-shock protein clpB of *Francisella tularensis* is involved in stress tolerance and is required for multiplication in target organs of infected mice. Mol Microbiol 2008; 67:1384-1401.

Quarry JE, Isherwood KE, Michell SL, Diaper H, Titball RW, Oyston PCF. A *Francisella tularensis* subspecies novicida pur F mutant, but not a purA mutant, induces protective immunity to tularemia in mice. Vaccine 2007; 25:2011-2018.

Saslaw S, Eigelsbach HT, Wilson HE, Prior JA, Carhart S. Tularemia vaccine study. I. Intracutaneous challenge. Arch Int Med 1961a; 107: 689-701.

Saslaw S, Eigelsbach HT, Prior JA, Wilson HE, Carhart S. Tularemia vaccine study II. Respiratory challenge. Arch Int Med 1961b; 107: 702-14.

Saslaw S, Carhart S. Studies with tularemia vaccines in volunteers. III. Serologic aspects following intracutaneous or respiratory challenge in both vaccinated and nonvaccinated volunteers. Am J Med Sci 1961; 241: 689-99.

Salomonsson E, Kuoppa K, Forslund A-L, Zingmark, C, Golovliov I, Sjostedt A, et al. (2009). Reintroduction of two deleted virulence loci restores full virulence to the live vaccine strain of *Francisella tularensis*. Infect Immun 2009; 7: 3424-31.

Sebastian S, Dillon ST, Lynch JG, Blalock _L-A T, Balon E, Lee KT, et al. A defined O-antigenpolysaccharide mutant of *Francisella tularensis* live vaccine strain has attenuated virulence while retaining its protective capacity. Infect Immun 2007; 75: 2591-2602.

Sjostedt A. Tularemia: History, epidemiology, pathogen physiology and clinical manifestations. Ann New York Acad Sci 2007; 1105: 1-29.

Tempel R, Lai XH, Crosa L, Kozlowicz B, Heffron F. Attenuated *Francisella novicida* transposon mutants protect mice against wild-type challenge. Infect Immun 2006; 74:5095-105.

Thomas RM, Titball RW, Oyston PCF, Griffin K, Waters E, Hitchen PG et al. The Immunologically Distinct O Antigens from *Francisella tularensis Subspecies tularensis* and *Francisella novicida* Are both Virulence Determinants and Protective Antigens. Infect Immun 2007; 75:371-378.

Twine SM, Bystrom M, Chen W, Forsman M, Golovliov IR, Johansson A, et al. A mutant of *Francisella tularensis* strain SCHU S4 lacking the ability to express a 58 kDa protein is attenuated for virulence and an effective live vaccine. Infect Immun 2005; 73:8345-52.

Twine S M. Petit M, Shen H, Mykytczuk N C S, Kelly J F, Conlan J W. (2006). Immunoproteomic analysis of the murine antibody response to successful and failed immunization with live anti-*Francisella* vaccines. Biochem Biophys Res Commun 2006; 346: 999-1008.

Woolard M D, Hensley L L, Kawula T H, Frelinger J A.et al. (2008). Respiratory *Francisella tularensis* Live Vaccine Strain Infection Induces Th17 Cells and Prostaglandin E2, Which Inhibits Generation of Gamma Interferon-Positive T Cells. Infect. Immun. 2008; 76: 2651-59.

Wu TH, Hutt JA, Garrison KA, Berliba LS, Zhou Y, Lyons CR. 2005. Intranasal vaccination induces protective immunity against intranasal infection with virulent *Francisella tularensis* biovar A. Infect Immun 2005; 73: 2644-54.

\* cited by examiner

```
ATGGATATAAATAAATTTACAATAAAACTACAAGAAGCTCTAGCTGAGGCTCAATCT
TATGCTTTTCAACAAAAAGCAACTGAGTTTACATCAGCACATATACTAAAAGCTCTTT
TGGAGCAAAATGATAGTGTTGCTATATCTATATTAAGCGTTTGTGGTGTTAATATAC
AAAACTTTATAAAAGCTGTAAATGATATGGTTGATAGTGTTGCGGTATTATCTGGAG
AAGGTAACCCTCAAGTAACACCATCTAGAGATTTAATAGCTACATTACATAAAATGC
AAGGGCTTGCTAATAAAAATGGTGATGAGTTTATCTCGAGTGAGGTTTTCTTATTAG
CCTCTTTAGAAGACAAAAGTTTAACTGGACTGTATAACAAATTTGGTATTACAAAAG
AAAAATTAACAAAAGCAGTCAATGATTATCGCGGAGGGGAGAAAGTGAGTAGTCAA
AATCAAGAAGATATGAAAGGTGCATTAGATAAATACACGGTAGATCTAACTGATCTA
GCGAGAAAAGGAAAAATTGATCCAATAATCGGTAGAGATAGTGAGATCCGTAGAAC
TATTCAAGTATTACAAAGAAGAACTAAGAACAACCCTGTGCTTATAGGTGAGCCTG
GTGTTGGTAAAACTGCTATTGTTGAGGGCTTAGCTCAACGAATAGTTAATGATGAA
GTACCAGAAGGTGTCAAAGGTAAAAAGTACTATCATTAGATATGGGTGCACTGCT
AGCTGGTGCTAAATTTAGAGGAGATTTTGAAGAGCGTCTAAAATCTGTATTAAAAGA
GTTATCAAAACAAGAAGGTAATGTAATTCTCTTTATAGATGAATTACATACTATGGTA
GGTGCTGGTAAAGCAGAAGGATCTATGGATGCTGGTAACATGCTTAAACCTGCTCT
AGCTAGAGGAGAGCTAAAGTGTGTTGGTGCAACAACTTTAGATGAGTATCGTGAGT
ATGTTGAAAAAGATCCGGCACTTGAGCGAAGATTCCAGAAAGTGCTAGTTGATGAA
CCTACTGTAGAAGATACTATCGCTATACTTAGAGGCCTAAAAGAAAGATATGAGCTA
CATCATGGTGTAAATATCACAGATTCAGCTATTGTAAGTGCAGCAACTTTGTCACAT
AGGTATATCACAGATAGACAGCTACCTGATAAAGCTATAGATCTAGTAGATGAAGC
AGCAAGCCAAATTCGTATGGAAATAGACTCTAAACCTGAAAAAATGGAAAGCTTATA
TCGTAGAATCATCCAGCTGAAAATGCAACGCGAACAGCTAAAGAAAGAGAAAGATG
ATGCTACTAAAAAACGTTTAGAGATACTTGAGCAAGAAATAAAAGGGCTAGACTCC
GAGTATAAAGGACTAGAAGAGCTTTGGAAAGCTGAAAAGCTTAAGATGCAAGGTAC
AAGTAAACTAAAAGAAGAGCTTGAGAAAGCCAAGTTTGAACTTGAAAAGTACCAAA
GAGTGGGTGATTTGAGCAAAATGGCAGAATTACAATACGGTAAAATACCTGAGCTA
GAAGCACAAATTAAACAAATAGAAGAAACTGAAGCAGAACCTTCTGAAAACAAATTA
GTAAGAACATCTGTTACAGAAAATGAGATTGCTGATGTAGTTTCAAAAGCTACTGGA
ATACCTGTGTCTAAGATGATGGAAGGCGAAAAAGACAAGCTTCTAAATATGGAAAG
TTTCTTACATAAAAGAGTAATCGGACAAGATCAAGCTATAAAAGCAGTATCAAATGC
TGTAAGAAGATCTCGTTCTGGATTATCAGATCCAAATAGACCTATAGGCTCATTCAT
GTTCTTAGGTCCAACTGGTGTCGGTAAAACTGAGCTTACAAAAGCTTTAGCAGAGT
TTTTGTTTGATGATGAAGATGCCATGCTTAGAGTAGATATGTCTGAGTTTATGGAGA
AACATTCTGTAGCTAGACTAATAGGCGCACCTCCTGGATACGTAGGTTATGAACAA
GGCGGCTATCTAACTGAACATGTTAGAAGAAAACCTTATTCTGTAATCTTACTTGAT
GAGGTTGAAAAAGCTCATGCTGATATATTTAACATCTTACTACAAGTGCTTGACGAT
GGTCGCCTAACAGATGGGCAAGGCAGAACAGTAGACTTTAAAAATACTGTAATAGT
TATGACTTCTAACCTTGGTTCACATCGAATCCAAGAAATGCAAGGTCAGGATTATGA
AACAGTAAAATCTGCTGTAATGGAAATGGTACTTAGCCACTTTAGACCTGAATTTGT
AAATAGAGTTGATGATGCAATTGTCTTTGAACCTCTAAACAAAGAGATGATAACTGA
AATAGCTAAAATACAAATCAAACGCTTAGAAAAACGTCTAGCAGATCTAAGTATAGG
ATTAGAAGTCACAACTGGAGCTATGGATAAACTAGCTGATGCTGGCTTTGATCCTG
TGTTTGGTGCTAGACCGCTTAAGCGCGCTATTCAAAACAACTTAGAAAACCCTCTG
GCTCTAAAACTTCTAGATGGTGAGTTTAAAGCTGAAGATAAAATAGTTGTCGATATT
GACGCTAATAACAATATTATATTCTCTAAATAA
```

FIG. 1

SEQUENCE LISTING

```
<160> NUMBER OF SEQ ID NOS: 1

<210> SEQ ID NO 1
<211> LENGTH: 2580
<212> TYPE: DNA
```

<213> ORGANISM: Francisella tularensis

<400> SEQUENCE: 1

| | | | | | |
|---|---|---|---|---|---|
| atggatataa | ataaatttac | aataaaacta | caagaagctc | tagctgaggc | tcaatcttat | 60 |
| gcttttcaac | aaaaagcaac | tgagtttaca | tcagcacata | tactaaaagc | tcttttggag | 120 |
| caaaatgata | gtgttgctat | atctatatta | agcgtttgtg | gtgttaatat | acaaaacttt | 180 |
| ataaaagctg | taaatgatat | ggttgatagt | gttgcggtat | tatctggaga | aggtaaccct | 240 |
| caagtaacac | catctagaga | tttaatagct | acattacata | aaatgcaagg | gcttgctaat | 300 |
| aaaaatggtg | atgagtttat | ctcgagtgag | gtttttcttat | tagcctcttt | agaagacaaa | 360 |
| agtttaactg | gactgtataa | caaatttggt | attacaaaag | aaaaattaac | aaaagcagtc | 420 |
| aatgattatc | gcggagggga | gaaagtgagt | agtcaaaatc | aagaagatat | gaaaggtgca | 480 |
| ttagataaat | acacggtaga | tctaactgat | ctagcgagaa | aaggaaaaat | tgatccaata | 540 |
| atcggtagag | atagtgagat | ccgtagaact | attcaagtat | tacaaagaag | aactaagaac | 600 |
| aaccctgtgc | ttataggtga | gcctggtgtt | ggtaaaactg | ctattgttga | gggcttagct | 660 |
| caacgaatag | ttaatgatga | agtaccagaa | ggtgtcaaag | gtaaaaaagt | actatcatta | 720 |
| gatatgggtg | cactgctagc | tggtgctaaa | tttagaggag | attttgaaga | gcgtctaaaa | 780 |
| tctgtattaa | aagagttatc | aaaacaagaa | ggtaatgtaa | ttctctttat | agatgaatta | 840 |
| catactatg | taggtgctgg | taaagcagaa | ggatctatgg | atgctggtaa | catgcttaaa | 900 |
| cctgctctag | ctagaggaga | gctaaagtgt | gttggtgcaa | caactttaga | tgagtatcgt | 960 |
| gagtatgttg | aaaaagatcc | ggcacttgag | cgaagattcc | agaaagtgct | agttgatgaa | 1020 |
| cctactgtag | aagatactat | cgctatactt | agaggcctaa | agaaagata | tgagctacat | 1080 |
| catggtgtaa | atatcacaga | ttcagctatt | gtaagtgcag | caactttgtc | acataggtat | 1140 |
| atcacagata | gacagctacc | tgataaagct | atagatctag | tagatgaagc | agcaagccaa | 1200 |
| attcgtatgg | aaatagactc | taaacctgaa | aaaatggaaa | gcttatatcg | tagaatcatc | 1260 |
| cagctgaaaa | tgcaacgcga | acagctaaag | aaagagaaag | atgatgctac | taaaaaacgt | 1320 |
| ttagagatac | ttgagcaaga | aataaaaggg | ctagactccg | agtataaagg | actagaagag | 1380 |
| cttttggaaag | ctgaaaagct | taagatgcaa | ggtacaagta | aactaaaaga | agagcttgag | 1440 |
| aaagccaagt | ttgaacttga | aaagtaccaa | agagtgggtg | atttgagcaa | atggcagaa | 1500 |
| ttacaatacg | gtaaaatacc | tgagctagaa | gcacaaatta | aacaaataga | agaaactgaa | 1560 |
| gcagaacctt | ctgaaaacaa | attagtaaga | acatctgtta | cagaaaatga | gattgctgat | 1620 |
| gtagtttcaa | aagctactgg | aatacctgtg | tctaagatga | tggaaggcga | aaaagacaag | 1680 |
| cttctaaata | tggaaagttt | cttacataaa | agagtaatcg | gacaagatca | agctataaaa | 1740 |
| gcagtatcaa | atgctgtaag | aagatctcgt | tctggattat | cagatccaaa | tagacctata | 1800 |
| ggctcattca | tgttcttagg | tccaactggt | gtcggtaaaa | ctgagcttac | aaaagcttta | 1860 |
| gcagagtttt | tgtttgatga | tgaagatgcc | atgcttagag | tagatatgtc | tgagtttatg | 1920 |
| gagaaacatt | ctgtagctag | actaataggc | gcacctcctg | gatacgtagg | ttatgaacaa | 1980 |
| ggcggctatc | taactgaaca | tgttagaaga | aaaccttatt | ctgtaatctt | acttgatgag | 2040 |
| gttgaaaaag | ctcatgctga | tatatttaac | atcttactac | aagtgcttga | cgatggtcgc | 2100 |
| ctaacagatg | ggcaaggcag | aacagtagac | tttaaaaata | ctgtaatagt | tatgacttct | 2160 |
| aaccttggtt | cacatcgaat | ccaagaaatg | caaggtcagg | attatgaaac | agtaaaatct | 2220 |
| gctgtaatgg | aaatggtact | tagccacttt | agacctgaat | ttgtaaatag | agttgatgat | 2280 |

```
gcaattgtct ttgaacctct aaacaaagag atgataactg aaatagctaa aatacaaatc    2340
aaacgcttag aaaaacgtct agcagatcta agtataggat tagaagtcac aactggagct    2400
atggataaac tagctgatgc tggctttgat cctgtgtttg gtgctagacc gcttaagcgc    2460
gctattcaaa acaacttaga aaaccctctg gctctaaaac ttctagatgg tgagtttaaa    2520
gctgaagata aaatagttgt cgatattgac gctaataaca atattatatt ctctaaataa    2580
```

MUTANTS OF *FRANCISELLA TULARENSIS* AND USES THEREOF

CROSS-REFERENCE TO RELATED APPLICATIONS

This application is a national phase entry of International Patent Application PCT/CA2010/000637 filed Apr. 23, 2010, which claims the benefit of U.S. Provisional Patent Application Ser. No. 61/213,030 filed Apr. 29, 2009.

FIELD OF THE INVENTION

The present invention relates to mutants of *Francisella tularensis* and uses thereof. More specifically, the present invention is directed to clpB mutants of *F. tularensis*.

BACKGROUND OF THE INVENTION

*Francisella tularensis* is a facultative intracellular bacterial pathogen that causes a spectrum of diseases collectively called tularemia. Two subspecies, subsp. *tularensis* (type A) and subsp. *holarctica* (type B) can cause severe disease in humans. In particular, inhalation of small numbers of type A *F. tularensis* has a mortality rate of 30-60% if left untreated (Sjostedt, 2007). In contrast, type A *F. tularensis* infections initiated by non-respiratory routes are far less lethal, and type B infections initiated by any route can cause debilitating, but non-life-threatening disease in humans.

An empirically attenuated type B strain of *F. tularensis* developed more than 50 years ago, *F. tularensis* live vaccine strain (LVS), has been used to protect against exposure to virulent type A strains of the pathogen. In formal testing using human volunteers, LVS was shown to impart complete protection against transdermal challenge with the type A strain SCHU S4, though it afforded lesser protection against an aerosol challenge (Saslaw et al 1961a, 1961b). It is the sole vaccine to have been formally shown to possess these properties. Due to safety concerns, it has never been fully licensed by the U.S. Food and Drug Administration (FDA).

Genomic sequencing of clinical type A and type B strains of *F. tularensis* as well as LVS allowed identification of the genetic modifications in the vaccine strain. Much of the attenuation of LVS versus clinical type B strains appears to be due to defects in a pilus gene, pilA, and a gene (FTT0918) of unknown function (Salomonsson et al. 2009). LVS also contains multiple other minor mutations that, separately or collectively, contribute to its attenuation.

LVS is known to elicit both an antibody response and a CD4+ and CD8+ T-cell response to several *F. tularensis* proteins. Experiments in mice indicate that the ability of LVS to elicit CD4+ and CD8+ T-cells secreting interferon gamma accounts for its efficacy against type A strains (Conlan et al. 2005; Wu et al. 2005). However, C57BL/6 mice that produce both antibodies and gamma interferon-secreting T-cells (Woolard et al. 2008; Twine et al 2006) following vaccination with LVS are not protected from challenge with type A bacteria (Chen et al. 2003, Wu et al 2005; Green, et al. 2005). Ignorance of the mechanism of protection of LVS and of the relative contributions of each of its mutations to its overall attenuation are major barriers to its full licensure by the U.S. FDA. The antigens of LVS that are responsible for eliciting protective immunity are unknown; additionally, because LVS is a vaccine generated from a type B strain, virulence factors and other macromolecules unique to type A strains are missing. These facts render difficult the task of designing specific antigen-based vaccines.

In recent years, various mutagenesis strategies have been used to identify virulence factors of *Francisella* that could be disrupted to produce novel live vaccine strains. Much of this work has been performed using LVS or *F. novicida*, a related subspecies of the pathogen that is only virulent for immunosuppressed humans. This approach relies on two critical assumptions regarding the use of LVS or *F. novicida* as surrogate clinical strains: 1) genes that are required for virulence of LVS or *F. novicida* predict virulence genes for clinical isolates; and 2) vaccines that protect against LVS or *F. novicida* will predictably protect against clinical strains.

However, LVS is already approximately 1,000,000-fold less virulent than clinical type A and B strains of the pathogen; thus, inhibiting the expression of any other virulence genes in LVS will only have an incremental effect on virulence. This renders impossible the prediction of effect any such mutation would have on a fully-virulent strain of *F. tularensis* in the absence of the innate mutations of LVS. Furthermore, it has been shown that mutant strains of LVS or *F. novicida* are able to protect mice against challenge with the homologous wild-type strain, but not against challenge with fully virulent type A bacteria (Quarry et al 2007; Sebastian et al 2007). Additionally, antibodies against surface lipopolysaccharides protect against *F. novicida* and type B strains, but fail to protect against Type A bacteria (Conlan et al 2002; Fulop et al 2001; Thomas et al. 2007). Finally, there appears to be no correlation between protection and vaccine-elicited antibody titre (Saslaw and Carhart 1961).

Furthermore, vaccines composed of killed cells and fractions thereof are sub-optimally effective against *F. tularensis* because such preparations fail to generate robust and prolonged protective cell-mediated immunity. Hence, there is currently no FDA-approved vaccine for general use that can provide prophylactic protection against respiratory tularaemia.

SUMMARY OF THE INVENTION

The present invention relates to mutants of *Francisella tularensis* and uses thereof. More specifically, the present invention is directed to clpB mutants of *F. tularensis*.

The present invention provides a mutant *F. tularensis* strain wherein the clpB gene is inactivated. The mutant *F. tularensis* strain may be attenuated. The mutant *F. tularensis* as just described may be derived from a *F. tularensis* strain selected from the group consisting of SCHU S4, FSC033, or FSC108, and FSC200.

The mutant *F. tularensis* strain as described may comprise a deleted clpB gene. The mutant *F. tularensis* strain as just described may also comprise other inactivated genes, for example, those selected from the group consisting of capB, wbtC, ggt, and fupA, or any combination thereof. In another embodiment, the mutant *F. tularensis* strain may be the mutant of CCUG deposit number CCUG 59672.

The present invention also provides a composition comprising a mutant *F. tularensis* strain wherein the clpB gene is inactivated, as described above. The composition may be an anti-*Francisella* vaccine composition. The composition may also comprise a pharmaceutically acceptable diluent, carrier, or excipient. The mutant *F. tularensis* strain in the composition as described above may be alive.

The present invention further provides a method of conferring immunity against *F. tularensis* comprising administering a mutant *F. tularensis* strain wherein the clpB gene is inactivated, or a composition comprising such a mutant. The administration of the mutant or composition may be done intradermally (ID), subcutaneously, by scarification, intramuscularly, orally, or by inhalation. The host may be an animal or a human. The method as described above may also comprise a step of boosting (i.e., a second administration) subsequent to the first administration of the mutant *F. tularensis* strain.

Additionally, the present invention provides a method of producing a mutant *F. tularensis* strain as described above. The method may comprise the steps of:
  a) obtaining cells of a virulent *F. tularensis* strain;
  b) inactivating the clpB gene;
  c) selecting for viable cells with attenuated virulence and clpB inactivation; and
  d) isolating the cells with attenuated virulence and clpB inactivation.

The Examples herein show that a mutant strain of *F. tularensis* SCHU S4 with a disrupted clpB gene is less virulent and more effective than LVS. When delivered orally or intradermally, the SCHU S4ΔclpB strain protects mice more effectively than LVS against aerosol challenge with wild-type bacteria. Thus, SCHU S4ΔclpB can be considered a candidate vaccine against clinical tularemia. Deletion of one or more additional virulence genes from SCHU S4ΔclpB to further protect against reversion is encompassed by the present invention.

Additional aspects and advantages of the present invention will be apparent in view of the following description. The detailed description and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

These and other features of the invention will now be described by way of example, with reference to the appended drawings, wherein:

FIG. 1 shows the DNA sequence of the clpB gene from *F. tularensis* strain SCHU S4 (SEQ ID NO: 1). The sequence comprises 2577 nucleotides. The clpB gene encodes a putative 859 amino acid protein (Entrez Protein identification CAG46402.1) of molecular weight 95,929 kD.

DETAILED DESCRIPTION OF THE INVENTION

Figure 2:
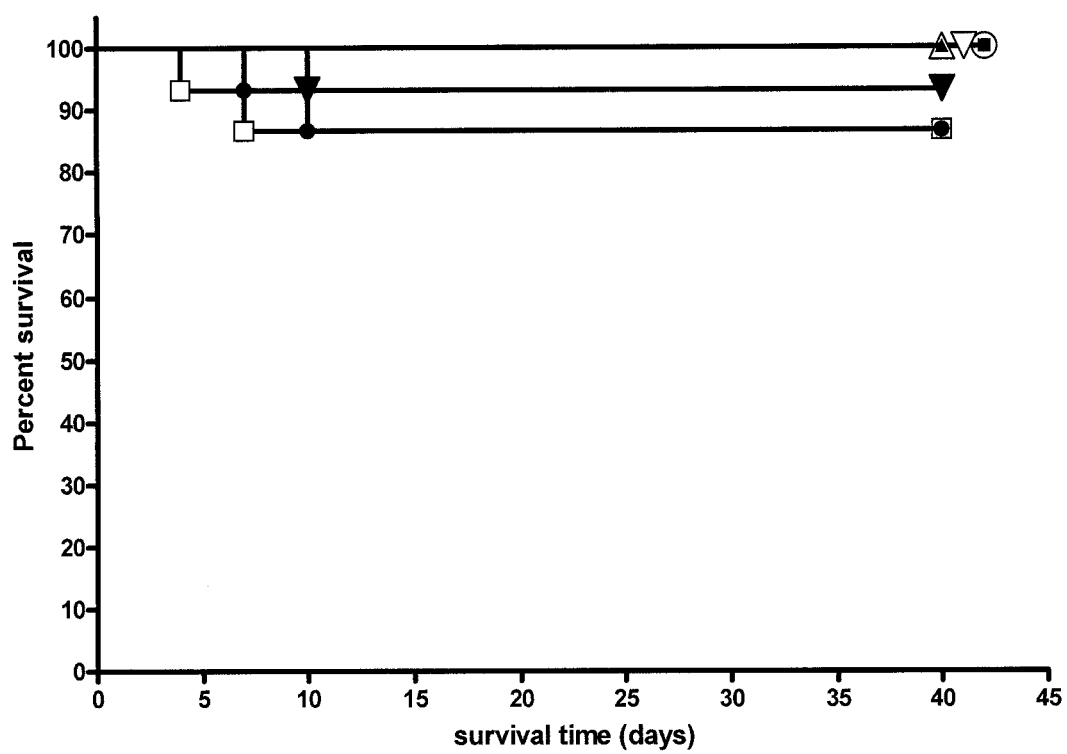
FIG. 2 is a graph showing the survival of BALB/c (open symbols) and C3H/HeN (closed symbols) after ID immunization with $10^5$ CFU of LVS (squares), SCHU AV (circles), SCHU S4ΔclpB (inverted triangles), or SCHU S4ΔiglC (triangles).

The present invention relates to mutants of *Francisella tularensis* and uses thereof. More specifically, the present invention is directed to clpB mutants of *F. tularensis*.

In one aspect, the present invention provides a mutant *F. tularensis* strain wherein the clpB gene is inactivated. The mutant *F. tularensis* strain may be attenuated. The mutant *F. tularensis* strain as just described may also comprise other inactivated genes.

*Francisella tularensis* is a facultative intracellular bacterial pathogen that causes a spectrum of diseases collectively called tularemia. The *F. tularensis* strain referred to above may be a type A (subspecies *tularensis*) or type B (subspecies *holarctica*) strain; in a specific non-limiting example, the *F. tularensis* strain may be a type A strain. Any suitable wild-type clinical strain of *F. tularensis* strain known in the art may be used to derive the mutant strain of the present invention; for example, but not wishing to be limiting, the *F. tularensis* strain may be SCHU S4, FSC033, or FSC108, or FSC200. In a specific, non-limiting example, the mutant may be derived from clinical *F. tularensis* strain SCHU S4.

The mutant *F. tularensis* strain of the present invention comprises an inactivated clpB gene. This gene encodes a heat shock protein that, without wishing to be bound by theory, may shield the pathogen from the environmental stresses it faces in the infected host. The gene may be "inactivated" by any suitable manner known in the art. For example, and not wishing to be limiting, the clpB gene may be inactivated by its complete or partial deletion from the *F. tularensis* strain (using methods known in the art, for example as described by Golovliov et al (2002)), by an inactivation mutation such as a multiple nucleotide substitution, or by an inactivating insertion such as a transposon insertion (using methods known in the art, for example those described by Kadzhaev et al (2009)). In a specific, non-limiting example, the clpB gene may be inactivated by complete deletion from the mutant strain. It is noted, however, that only those methods which result in inactivation of the clpB gene are encompassed by the present invention. The inactivation of the clpB gene may result in complete or partial attenuation of the mutant *F. tularensis* strain.

By the term "attenuation" or "attenuated", it is meant that the pathogen is kept live, but exhibits reduced virulence such that it does not cause the disease caused by the virulent pathogen. The attenuation of the particular strain of the present invention may result from the inactivation of the clpB gene, or may be the result of other mechanisms for attenuation, for example and not limited to mutagenesis, deletion or inactivation of targeted genes, or natural attenuation. In an non-limiting embodiment, attenuation of the strain may be conferred by a combination of the aforementioned factors.

In a specific, non-limiting example, the mutant *F. tularensis* strain may be the mutant of CCUG deposit number CCUG 59672.

The mutant *F. tularensis* strain of the present invention may further comprise additional inactivated genes. The additional inactivated gene may be a virulence gene (i.e., a gene that contributes to the virulence of the pathogen), or may be any other type of gene. For example, but not intending to be limiting in any manner, one or more than one other virulence gene may be inactivated to prevent reversion and/or may contribute to attenuation of the mutant *F. tularensis* strain. In a specific non-limiting example, the one or more than one additional inactivated gene may be selected from the capB, wbtC, ggt, and fupA gene panel, or a combination thereof. The additional inactivated genes may show no additional effect of attenuation of the mutant *F. tularensis* strain, or may contribute to attenuation of the strain.

The present invention further provides a method of producing the mutant *F. tularensis* strain as described herein. The method may comprise the steps of:
 a) obtaining cells of a virulent *F. tularensis* strain;
 b) inactivating the clpB gene;
 c) selecting for viable cells with attenuated virulence and clpB inactivation; and
 d) isolating the cells with attenuated virulence and clpB inactivation.

The virulent *F. tularensis* strain provided in step a) of the presently described method may be any suitable virulent strain known in the art; the strain should be "virulent" in that it may cause any disease in the spectrum referred to as tularaemia, whether mild or severe. The virulent *F. tularensis* strain may be SCHU S4, FSC033, or FSC108, or FSC200. In a specific, non-limiting example, the *F. tularensis* strain may be SCHU S4. In an alternative, the *F. tularensis* strain in step a) may be a mutant *F. tularensis* strain, wherein the mutations may have been introduced to attenuate the pathogen (either partially or completely) or for other purpose.

In step b), the clpB gene may be inactivated using any suitable technique known in the art; for example, and without wishing to be limiting in any manner, the gene may be inactivated by its complete or partial deletion from the *F. tularensis* strain, by an inactivation mutation such as a multiple nucleotide substitution, or by an inactivating insertion such as a transposon insertion. In a specific, non-limiting example, the clpB gene may be inactivated by its complete deletion.

In steps c) and d), the cells with attenuated virulence and clpB inactivation are selected and isolated, respectively. These steps may be performed using any known, suitable method; for example, and without wishing to be limiting in any manner, the method of selecting may be performed using animal models. Methods of isolating and selecting the cells/strains are well-known to those of skill in the art; for example, and without wishing to be limiting in any manner, methods of selecting and isolating are described by Kadzhaev et al (2009) and Golovliov et al (2002).

In another aspect, the present invention provides a composition comprising a mutant *F. tularensis* strain wherein the clpB gene is inactivated, as described above. The composition may be an anti-*Francisella* vaccine composition. In addition to the mutant *F. tularensis* strain, the composition may comprise a pharmaceutically acceptable diluent, excipient, or carrier. The diluent, excipient, or carrier may be any suitable diluent, excipient, or carrier known in the art, and must be compatible with other ingredients in the composition, with the method of delivery of the composition, and is not deleterious to the recipient of the composition. The composition may be in any suitable form; for example, the composition may be provided in suspension form, powder form (for example, lyophilised), capsule or tablet form. For example, and without wishing to be limiting, when the composition is provided in suspension form, the carrier may comprise water, saline, a suitable buffer, or additives to improve solubility and/or stability; reconstitution to produce the suspension is effected in a buffer at a suitable pH to ensure the viability of the bacteria. In a specific, non-limiting example, the pharmaceutically acceptable carrier may be saline. Dry powders may also include additives to improve stability and/or carriers to increase bulk/volume; for example, and without wishing to be limiting, the dry powder composition may comprise sucrose or trehalose. It would be within the competency of a person of skill in the art to prepare suitable compositions comprising the present compounds.

Yet another aspect of the present invention is directed to a method of conferring immunity against *F. tularensis* comprising administering a mutant *F. tularensis* strain wherein the clpB gene is inactivated, or a composition containing such mutant. The mutant *F. tularensis* strain may be administered by any suitable route know in the art. For example, and not wishing to be limiting, the mutant *F. tularensis* strain may be administered intradermally (ID), subcutaneously, by scarification, intramuscularly, orally, or by inhalation. The method may comprise a step of boosting subsequent to the initial administration of the mutant *F. tularensis* strain. This second administration of mutant *F. tularensis* strain may be done using the same or a different route of administration. The second administration may also be given at any suitable time interval; for example and not wishing to be limiting, the boost may be given 4 to 52 weeks following the initial administration; for example, and without wishing to be limiting, the booster may be administered 4, 8, 12, 20, 26, 32, 38, 44, or 52 weeks following the initial administration or any time therebetween. In a specific, non-limiting example, the booster may be administered 8 weeks after the initial administration.

The mutant *F. tularensis* strain may be used to vaccinate a host; the host may be a human host or an animal host. The dosage for administration will be dependent on various factors, including the size and weight of the host and the specifics of the composition formulated. Based on experience with LVS, and without wishing to be limiting in any manner, a dose of approximately $10^7$ CFU may be used for administration to humans. It would be within the capabilities of persons of skill in the art to determine appropriate dosages for vaccination.

Infections of humans with type A strains of *F. tularensis* are rare, thus making it difficult to conduct Phase III clinical trials to determine the efficacy of novel anti-*Francisella* vaccines. Instead, the FDA has devised a policy, the Animal Rule (http://www.fda.gov/cber/rules/humeffic.htm; also see Federal Register: May 31, 2002 (Volume 67, Number 105, pages 37988-37998)), which permits approval of anti-*Francisella* vaccines based on efficacy studies performed exclusively with animal models. The Animal Rule requires that any such animal models should mimic the human disease, and that vaccine-elicited protection in animals should predict efficacy in humans.

Previously published studies have shown that deleting the clpB gene from LVS or *F. novicida* resulted in attenuation (Meibom et al 2008, Tempel et al 2006). It has also been shown that LVS with a disrupted clpB gene protects mice against intraperitoneal challenge with the highly attenuated wild-type LVS (Meibom et al 2008). However, these findings cannot be used to predict the efficacy of such a mutant against challenge with a type A strain via the IP or any other route. Nor can they be used to predict the phenotype of a type A strain with a defective clpB gene.

The virulence of LVS is reduced by >99.9999% (=1,000,000-fold less) to that of clinical type A and B strains of the pathogen. Therefore, inhibiting the expression of additional virulence genes in LVS will have only an incremental effect on virulence. This cannot be used to predict what effect, if any, a mutation would have on a fully-virulent strain of *F. tularensis* in the absence of the background mutations present in LVS. For instance, it has been shown that deleting the katG gene from LVS further decreases its virulence for mice, but deleting the same gene from SCHU S4 did not affect its virulence (Lindgren et al 2007). Similar findings apply to the to/C and chi A genes (Kadzhaev, et al. 2009).

Additionally, antibodies against surface lipopolysaccharide alone are sufficient to protect mice from infection with LVS or *F. novicida*, but such antibodies fail to protect against type A bacteria (Conlan et al 2002, Fulop et al 2001; Thomas et al 2007). Similarly, mutant strains of LVS or *F. novicida* are able to protect mice against challenge with the homologous wild-type strain, but not against challenge with fully virulent type A bacteria (Quarry et al 2007; Sebastian et al 2007). Thus, it is not feasible to evaluate the effects of mutation of a Type A *F. tularensis* strain using the LVS or *F. novicida* models.

Thus, there is no clear manner of predicting a priori whether mutating a particular gene will attenuate type A *F. tularensis*. Moreover, mere attenuation of a type A strain does not predict its ability to act as a vaccine strain able to protect mice against challenge with the wild-type strain (Twine et al 2005; Conlan, et al. 2010).

The Examples herein show that a mutant strain of *F. tularensis* SCHU S4 with a disrupted clpB gene is less virulent and more effective than LVS by intradermal and oral routes of administration. By the intranasal route, it is shown that the lethal dose of SCHU S4ΔclpB is at least 100-fold higher than that of LVS. When delivered orally or intradermally, the SCHU S4ΔclpB strain protects mice much more effectively than LVS against aerosol challenge with wild-type bacteria. Thus, SCHU S4ΔclpB can be considered a highly defined candidate vaccine against clinical tularemia. Deletion of additional virulence genes from SCHU S4ΔclpB to further ensure against reversion is encompassed by the present invention.

The SCHU S4ΔclpB mutant was compared against LVS for its ability to elicit protection against pulmonary challenge following traditional ID vaccination (LVS is indicated for scarification administration only to humans). SCHU S4ΔclpB showed a level of attenuation similar to LVS (>1-million-fold versus wild-type SCHU S4 by the ID route) and was as effective as LVS at combating ID challenge with >1000 $LD_{50}$ of the fully virulent pathogen.

Against an aerosol challenge, SCHU S4ΔclpB was superior to LVS in both tested mouse strains. Moreover, only SCHU S4ΔclpB provided significant protection against aerosol challenge in both BALB/c and C3H/HeN mice when administered orally. Primary oral vaccination was inferior to ID vaccination for all test vaccines. However, oral boosting improved the efficacy of orally administered SCHU S4ΔclpB in C3H/HeN mice.

SCHU S4ΔclpB caused a sub-lethal infection in BALB/c mice when administered ID at a dose of $10^5$ CFU, that was similar to previous results obtained with LVS. However, this experiment revealed no obvious explanation for the superior protection against aerosol challenge elicited by SCHU S4ΔclpB. Instead, this correlated with an enhanced ability of mice immunized with it to control a subsequent aerosol challenge with SCHU S4. In this regard, immunization with LVS or SCHU S4ΔclpB effectively curtailed the bacteremia that develops during the final stage of primary lethal tularemia suggesting that this aspect of the infection contributes little to morbidity and mortality. Previously, it was shown that anti-LVS antibodies rapidly sequester LVS from the blood to the liver (Anthony and Kongshavn, 1987), and presumably, but without wishing to be bound by theory, the same mechanism is at work in the current study. However, it is generally believed that these antibodies play only a minor role in protection from pulmonary or systemic infection. Instead, specific CD4+ and CD8+ T-cells appear to be crucial for controlling these aspects of the infection.

During the first four days of infection, mice immunized with SCHU S4ΔclpB were better able than mice immunized with LVS to control pulmonary infection. Bacterial burdens in the liver and spleen were also significantly lower in the former mice; without wishing to be bound by theory, these mice may have better prevented dissemination to internal organs and/or controlled infection therein. By day 7, mice immunized with SCHU S4ΔclpB harboured 100-fold fewer bacteria in their lungs, and 1000-fold fewer bacteria in their livers and spleens than mice immunized with LVS.

Based on the results in animal models presented herein and on the FDA's Animal Rule, the mutant *F. tularensis* strain of the present invention constitutes an excellent candidate as an anti-*Francisella* vaccine for both animals and humans.

The present invention will be further illustrated in the following examples. However, it is to be understood that these examples are for illustrative purposes only and should not be used to limit the scope of the present invention in any manner.

EXAMPLE 1

Generating Bacterial Strains

The ATCC isolate 29684 of LVS was used for comparison with SCHU S4-based vaccines. Naturally-attenuated SCHU AV and deletion mutant SCHU S4ΔiglC have been previously described (Twine et al., 2005); these mutants were included as positive and negative SCHU S4-based vaccine controls, respectively.

New mutant strain SCHU S4ΔclpB was generated using art-known methods, generally described by Golovliov et al (2002). Briefly, an in-frame deletion of the clpB gene was constructed by allelic exchange based on integration and excision of a suicide plasmid carrying upstream and downstream sequences of the target gene. The upstream and downstream regions of the gene were amplified by PCR. The PCR fragments for the gene contained complementary sequences in the 3' end of the upstream fragment and the 5' end of the downstream fragment which were annealed during a second round of PCR. After restriction enzyme digestion and purification, the PCR fragments were cloned to the suicide vector pDMK2, which was later transformed to *Escherichia coli* S17-1. Conjugation to *F. tularensis* SCHU S4 was carried out as described previously (Golovliov et al 2002). Conjugants were selected on media containing 10 μg/ml kanamycin and 50 μg/ml of polymyxin B and confirmed by PCR. To select for a second recombination event, conjugants were plated on medium containing 5% sucrose and the deletion of the gene identified by PCR and the exact location verified by sequencing. The strategy led to the deletion of 2463 out of the 2580 bp for clpB. The clpB gene sequence (SEQ ID NO:1) is shown in FIG. 1.

For animal studies, stock cultures of all strains were prepared by growing them as confluent lawns on cystine heart agar supplemented with 1% (w/v) hemoglobin (CHAH). Bacteria were harvested after 48-72 h incubation at 37° C. into freezing medium comprising modified Mueller Hinton broth containing 10% w/v sucrose. Stocks were aliquoted volumes of 1 ml and stored at −80° C. at a concentration of $10^{10}$-$10^{11}$ CFU/mL.

The presently-generated mutant strain SCHU S4ΔclpB was deposited with the Culture Collection University of Gothenburg (CCUG; Sahlgrenska Academy of the University of Gothenburg, Box 7193, SE-402 34, Göteborg, Sweden); the deposit has been granted accession number CCUG 59672.

EXAMPLE 2

Efficacy of ID Vaccination Against Aerosol Challenge

The degree of protection against inhalation tularemia elicited by ID immunization with the mutant *F. tularensis* strain of Example 1 was examined.

The ID $LD_{50}$ for LVS is >$10^8$ CFU, and $10^5$ CFU administered ID protects against systemic but not aerosol challenge (Conlan et al 2003; Chen et al 2003). Therefore, $10^5$ CFU was chosen as the ID immunizing dose for all of the test vaccine strains, and BALB/c and C3H/HeN mice as the model hosts for determining their efficacy. ID inocula were injected into a fold of skin in the mid-belly in a volume of 0.05 ml saline. Aerosol challenges were performed six weeks post-vaccination with a low dose (~20 CFU) aerosol of type A strain SCHU S4 using an InTox Products nose-only exposure chamber as previously described (Conlan et al 2002). All animal work was performed in a federally-licensed and Select-Agent-approved small animal containment level 3 facilities. Mice were examined daily for signs of infection and whenever feasible were euthanized by $CO_2$ asphyxiation as soon as they displayed signs of irreversible morbidity.

It was previously shown that LVS, but not SCHU AV or SCHU S4ΔiglC at this dose elicited obvious necrosis at the site of injection and visible signs of infection (ruffled fur) in BALB/c mice (Twine et al 2005). In this regard, SCHU S4ΔclpB was similar to SCHU AV (data not shown). As expected from previous studies, LVS at an ID dose of $10^5$ CFU killed a few BALB/c (2/15) mice, whereas all C3H/HeN mice survived (FIG. 2). The reverse result was observed with SCHU AV which killed 2/15 C3H/HeN mice, but none of the BALB/c mice. Both mouse strains survived ID immunization with SCHU S4ΔclpB and SCHU S4 ΔiglC.

It has also been previously shown that BALB/c mice immunized ID with LVS or SCHU AV, but not SCHU S4ΔiglC survived a subsequent ID challenge with 1000 $LD_{50}$ of fully-virulent type A *F. tularensis* (Twine et al, 2005). SCHU S4ΔclpB protected against similar ID challenge (not shown). BALB/c mice immunized with SCHU S4ΔclpB were better protected against an aerosol challenge with SCHU S4, compared to mice immunized with LVS. Both vaccines were equally effective in C3H/HeN mice. Results are shown in Table 1.

TABLE 1

Survival of ID immunized mice following aerosol challenge with SCHU S4.

| Mouse strain | vaccine | Time to death of individual mice (days) | Median time to death (days) |
| --- | --- | --- | --- |
| BALB/c | none | 5, 5, 5, 5, 5, 5 | 5 |
| BALB/c | LVS | 7, 7, 8, 9, 12 | 8[1] |
| BALB/c | SCHU AV | 6, 9, 10, 10, 12 | 10[1] |
| BALB/c | SCHU S4ΔclpB | 8, 11, >28, >28, >28 | 19[1] |
| BALB/c | SCHU S4ΔiglC | 5, 5, 6, 6, 6 | 6 |
| C3H/HeN | none | 5, 5, 5, 5, 5, 5 | 5 |
| C3H/HeN | LVS | 9, 9, 11, 12, 14 | 11[1] |
| C3H/HeN | SCHU AV | 6, 6, 6, 7, >28 | 6[1] |
| C3H/HeN | SCHU S4 Δ clpB | 5, 8, 10, 11, 14 | 10[1] |
| C3H/HeN | SCHU S4 Δ iglC | 5, 5, 5, 6, 6 | 5 |

[1]significantly greater survival (P < 0.05 chi² comparison of survival curves) than for naive mice or mice immunized with SCHU ΔiglC All (n=6) naïve BALB/c and C3H/HeN mice died on day 5 of challenge and all mice (n=5) immunized with SCHU S4ΔiglC died on days 5 or 6. All other vaccine candidates elicited a statistically significant (P<0.02 comparison of survival curves by Chi square test) increase in median survival compared to naïve BALB/c mice or BALB/c mice immunized with SCHU S4ΔiglC. BALB/c mice immunized with SCHU S4ΔclpB showed the best median survival (19 days) and this was significantly (P<0.05) longer than the survival of BALB/c mice immunized with LVS. In C3H/HeN mice, LVS and SCHU S4ΔclpB elicited a statistically significant increase in survival compared to naïve mice or mice immunized with SCHU S4ΔiglC (p<0.02). LVS produced a slight improvement in median survival in C3H/HeN versus BALB/c mice challenged by aerosol with SCHU S4 (11 versus 8 days; P>0.05).

EXAMPLE 3

Efficacy of Oral Vaccination Against Aerosol Challenge

The degree of protection against inhalation tularemia elicited by oral immunization with the mutant *F. tularensis* strains of Example 1 was examined.

BALB/c mice have been shown to survive oral immunization with $10^8$ CFU of LVS and subsequently demonstrate some protection against aerosol challenge with type A *F. tularensis* (KuoLee et al 2007). For this reason, $10^8$ CFU was chosen as the oral immunizing dose for all of the test vaccine strains and BALB/c and C3H/HeN mice as the model hosts for determining their efficacy. For oral immunization, mice were gavaged once with a chosen vaccine strain suspended in 0.2 ml saline.

Most BALB/c mice immunized once orally with $10^8$ LVS have been shown to be fully protected against low dose aerosol challenge with type A *F. tularensis*, but this immunity wanes substantially after 4 weeks (KuoLee et al 2007). To determine whether the present vaccine strains might be superior to LVS in this regard, aerosol challenges were performed 6-weeks post vaccination, when LVS-elicited protection would be expected to have markedly diminished. Aerosol challenges were performed six weeks post-vaccination with a low dose (~20 CFU) aerosol of type A strain SCHU S4 using an InTox Products nose-only exposure chamber as previously described (Conlan et al 2002). All animal work was performed in a federally-licensed and Select-Agent-approved small animal containment level 3 facilities. Mice were examined daily for signs of infection, and whenever feasible were euthanized by $CO_2$ asphyxiation as soon as they displayed signs of irreversible morbidity.

Results are shown in Table 2.

TABLE 2

Survival of orally immunized mice following aerosol challenge with SCHU S4.

| Mouse strain | vaccine | Time to death of individual mice (days) | Median time to death (days) |
| --- | --- | --- | --- |
| BALB/c | none | 5, 5, 5, 5, 5, 5 | 5 |
| BALB/c | LVS | 5, 5, 5, 7, 7 | 5 |
| BALB/c | SCHU AV | 5, 5, 5, 5 | 5 |
| BALB/c | SCHU S4ΔclpB | 9, 9, 16, >28, >28 | 16[1] |
| BALB/c | SCHU S4ΔiglC | 5, 5, 5, 5, 5 | 5 |
| C3H/HeN | none | 5, 5, 5, 5, 5 | 5 |
| C3H/HeN | LVS | 4, 5, 5, 5, 5 | 5 |
| C3H/HeN | SCHU AV | 5, 5, 5, 5, 5 | 5 |

TABLE 2-continued

Survival of orally immunized mice following
aerosol challenge with SCHU S4.

| Mouse strain | vaccine | Time to death of individual mice (days) | Median time to death (days) |
|---|---|---|---|
| C3H/HeN | SCHU S4 ΔclpB | 5, 9, 12, 13, 16 | 12[1] |
| C3H/HeN | SCHU S4ΔiglC | 5, 5, 5, 6, 6 | 5 |

[1]significantly greater survival (P < 0.05) than for naive mice or mice immunized with SCHU Δ iglC.

Figure 3:
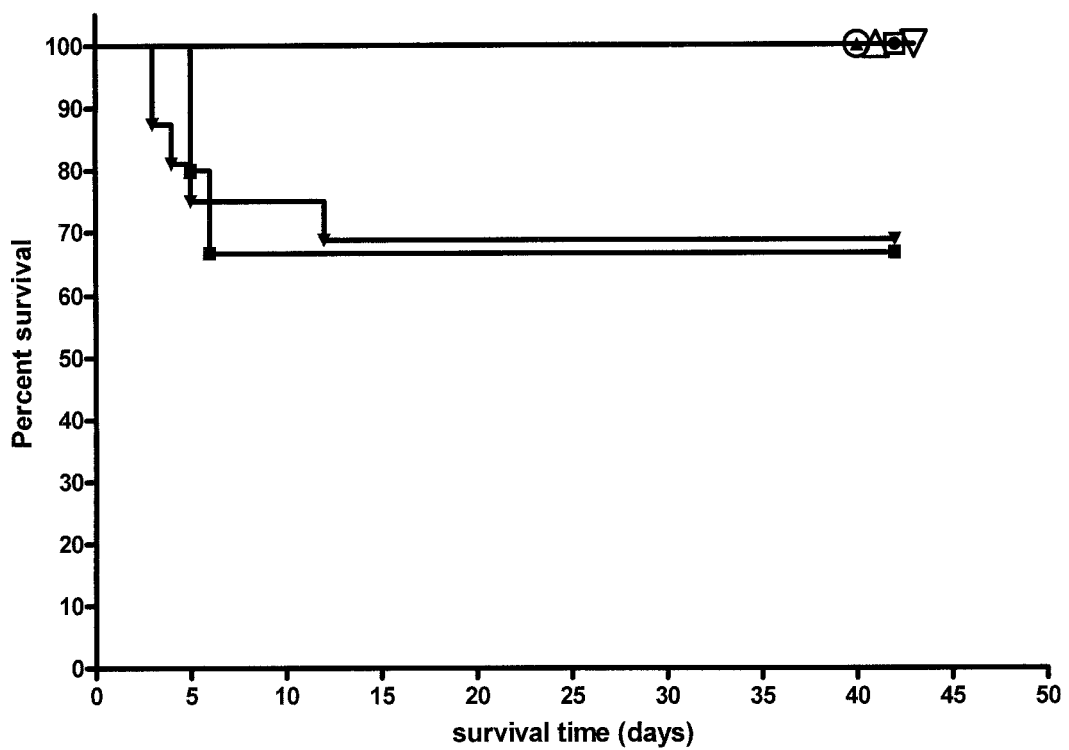
FIG. 3 is a graph showing the survival of BALB/c (open symbols) and C3H/HeN (closed symbols) after oral immunization with $10^8$ CFU of LVS (squares), SCHU AV (circles), SCHU S4ΔclpB (inverted triangles), or SCHU S4ΔiglC (triangles).

By this vaccination route, SCHU AV and SCHU S4 ΔiglC were completely avirulent for both BALB/c and C3H/HeN mice. Similarly, LVS and SCHU S4ΔclpB were completely attenuated for BALB/c mice, but each killed 5/15 C3H/HeN mice (FIG. 3).

All control mice died on day 5 of challenge, as did all C3H/HeN mice immunized with LVS or SCHU AV; 2/5 of C3H/HeN mice immunized orally with SCHU S4ΔiglC survived to day 6. All BALB/c mice immunized with SCHU AV or SCHU S4ΔiglC died on day 5, whereas 2/5 BALB/c mice immunized with LVS survived to day 7. In contrast, C3H/HeN and BALB/c mice immunized orally with SCHU S4 ΔclpB survived significantly longer than control mice (P<0.01).

EXAMPLE 4

Effect of Oral Boosting on Vaccine Efficacy

Eight weeks after ID or oral vaccination, as described in Examples 2 and 3, some mice were re-immunized orally with $10^8$ CFU of the homologous mutant strain. In contrast to primary oral immunization, no mice died following oral boosting. Six weeks post-boosting, mice were exposed to an aerosol of 20 CFU of SCHU S4 (as described above) and their survival was monitored (Tables 3 and 4). Oral boosting of ID immunized BALB/c mice did not improve survival compared to primary ID or oral vaccination. Indeed, protection appeared to have waned in the former mice. In contrast, oral boosting following oral immunization improved the median survival of C3H/HeN mice vaccinated with LVS or SCHU S4ΔclpB (of Example 1).

TABLE 3

Survival of ID immunized orally boosted mice following
aerosol challenge with SCHU S4.

| Mouse strain | vaccine | Time to death of individual mice (days) | Median time to death (days) |
|---|---|---|---|
| BALB/c | none | 5, 5, 5, 5, 5, 5 | 5 |
| BALB/c | LVS | 6, 7, 8, 8 | 7.5[1] |
| BALB/c | SCHU AV | 6, 6, 6, 6 | 6 |
| BALB/c | SCHU S4ΔclpB | 7, 9, 11, 11, >28 | 11[1] |
| BALB/c | SCHU S4ΔiglC | 5, 6, 6, 6 | 6 |
| C3H/HeN | none | 5, 5, 6, 6, 6, 6, | 6 |
| C3H/HeN | LVS | 5, 6, 7, 7, 7, 8 | 7 |
| C3H/HeN | SCHU AV | 5, 5, 6, 7 | 5.5 |
| C3H/HeN | SCHU S4ΔclpB | 8, 13, 16, 16, 19 | 16[1] |
| C3H/HeN | SCHU S4ΔiglC | 5, 6, 6, 6, 7 | 6 |

[1]significantly greater survival (P < 0.05) than for naive mice or mice immunized with SCHU S4ΔiglC.

TABLE 4

Survival of orally immunized orally boosted
mice following aerosol challenge.

| Mouse strain | vaccine | Time to death of individual mice (days) | Median time to death (days) |
|---|---|---|---|
| BALB/c | none | 5, 5, 5, 5, 5, 5 | 5 |
| BALB/c | LVS | 5, 6, 7, 8, 8 | 7[1] |
| BALB/c | SCHU AV | 5, 5, 5, 5, 5 | 5 |
| BALB/c | SCHU S4 Δ clpB | 5, 6, 11, 19, >28 | 11[1] |
| BALB/c | SCHU S4 Δ iglC | 5, 5, 5, 5, 5 | 5 |
| C3H/HeN | none | 5, 5, 5, 5, 5, 5 | 5 |
| C3H/HeN | LVS | 5, 6, 7, 8, 8 | 7[1] |
| C3H/HeN | SCHU AV | 5, 5, 5, 5, 5 | 5 |
| C3H/HeN | SCHU S4 Δ clpB | 11, 15, >28, >28, >28 | >28[1] |
| C3H/HeN | SCHU S4 Δ iglC | 5, 5, 5, 5, 5 | 5 |

[1]significantly greater survival (P < 0.05) than for naive mice or mice immunized with SCHU S4Δ iglC.

EXAMPLE 5

Course of Infection in Vaccinated Mice

The infection kinetics of LVS in ID immunized mice have been previously examined (Chen et al 2003). Therefore, the in vivo growth characteristics of SCHU S4ΔclpB were determined (Table 5).

The results of Examples 2 to 4 show that for SCHU S4-based vaccines neither oral immunization, nor boosting, nor the use of C3H/HeN mice conferred any survival advantage over a single ID immunization of BALB/c mice. Therefore, the remaining studies used only ID immunized BALB/c mice. Moreover, since SCHU S4ΔiglC elicited no protection, and SCHU AV was inferior to SCHU S4ΔclpB, these control groups were not pursued further.

The in vivo growth characteristics of SCHU S4ΔclpB (of Example 1) were determined and are shown in Table 5. Briefly, organs were removed at the stated times, homogenized in sterile saline, diluted and plated on CHAH medium. Colony counts were performed after 48-72 h incubation at 37° C. Overall in vivo growth kinetics of SCHU S4ΔclpB were similar to previously published results for LVS (Chen et al, 2003).

TABLE 5

In vivo growth of SCHU S4ΔclpB following ID
inoculation into BALB/c mice.

| | $Log_{10}$ ± SD bacterial burden on day post infection: | | | |
|---|---|---|---|---|
| Tissue | 2 | 4 | 7 | 16 |
| skin | 6.84 ± 0.17 | 5.49 ± 0.57 | 4.21 ± 0.44 | <1.30 (0/5) |
| spleen | 4.87 ± 0.36 | 6.49 ± 0.52 | 4.59 ± 0.14 | 3.69 ± 0.11 |
| liver | 4.55 ± 0.38 | 5.89 ± 0.33 | 4.63 ± 0.13 | 3.78 (1/5) |
| lungs | 1.78 (1/5) | 2.55 ± 0.70 | 3.47 ± 0.41 | <1.30 (0/5) |

N = 5 mice/group; ( ), proportion of organs infected used to calculate mean.

The course of infection initiated by inhalation of wild-type SCHU S4 in naïve and immunized mice was also examined using the methods described above (Table 6).

TABLE 6

In vivo growth of *F. tularensis* SCHU S4 following aerosol challenge of vaccinated mice.

| Vaccine group | Tissue | Log10 SD bacterial burden on day post-aerosol-challenge: | | | | |
|---|---|---|---|---|---|---|
| | | 2 | 4 | 7 | 10 | 14 |
| naïve | lungs | 6.09 ± 0.11 | 7.71 ± 0.20 | | | |
| LVS | | 6.0 ± 0.17 | 7.52 ± 0.07 | 8.31 ± 0.20 | | |
| ΔclpB | | 4.79 ± 0.93[1,2] | 5.94 ± 0.46[1,2] | 6.27 ± 0.96[2] | 6.91 ± 0.96 | 3.97 ± 1.83 |
| naïve | liver | 4.04 ± 0.88 | 7.99 ± 0.25 | | | |
| LVS | | 3.07 ± 0.58 | 5.77 ± 0.13[1] | 7.94 ± 0.73 | | |
| ΔclpB | | 1.87 (2/4)[1] | 4.26 ± 0.41[1,2] | 4.14 ± 0.64[2] | 5.33 ± 0.70 | 3.70 (3/4) |
| naïve | spleen | 3.85 ± 1.0 | 8.26 ± 0.98 | | | |
| LVS | | 2.13 ± 0.76[1] | 5.75 ± 0.17[1] | 7.54 ± 0.92 | | |
| ΔclpB | | 2.43 ± 0.46[1] | 3.76 ± 0.38[1,2] | 3.63 ± 0.58[2] | 4.52 ± 0.82 | 3.41 ± 1.43 |
| naïve | Blood/mL | 2.82 ± 0.94 | 7.19 ± 0.03 | | | |
| LVS | | 3.47 (1/4)[1] | 3.22 ± 0.87[1] | 4.22 (2/4) | | |
| ΔclpB | | 2.85 (1/4)[1] | 2.0 (1/4)[1] | 2.0 (1/4) | 4.38 (2/4) | <2.0 (0/4) |

Mice (n = 4/group);
[1]burden significantly lower than in naïve mice
[2]burden significantly lower than in LVS-immunized mice Both vaccines effectively conferred control of the intense bacteremia associated with primary infection. By day 2 of infection mice immunized with SCHU S4ΔclpB harbored significantly fewer bacteria in their lungs than naïve mice or mice immunized with LVS. On day 4 of infection, lung burdens were similar in naïve and LVS immunized mice, with burdens in mice immunized with SCHU S4ΔclpB at significantly lower levels. LVS-immunized mice harbored >100-fold fewer bacteria in their livers and spleens than naïve mice at day 4, and mice immunized with SCHU S4ΔclpB harbored significantly fewer bacteria than LVS-immunized mice. Naïve mice did not survive beyond day 5. On day 7 of infection, mice immunized with LVS harbored a bacterial load in the lungs that was significantly higher than the burden in the lungs of mice immunized with SCHU S4ΔclpB. At this time, mice immunized with SCHU S4ΔclpB were better controlling infection in the liver and spleen than LVS-immunized mice. No LVS immunized mice survived to day 10 of infection. At day 10, mice immunized with SCHU S4ΔclpB harboured similar numbers of bacteria in the lungs, liver and spleen as at day 7. Only between days 10-15 did these mice begin to reduce the bacterial burden in the lungs to the low levels seen in the liver and spleen throughout the course of infection.

EXAMPLE 6

Survival of ID Immunized Mice Against Intranasal Challenge

Figure 4:
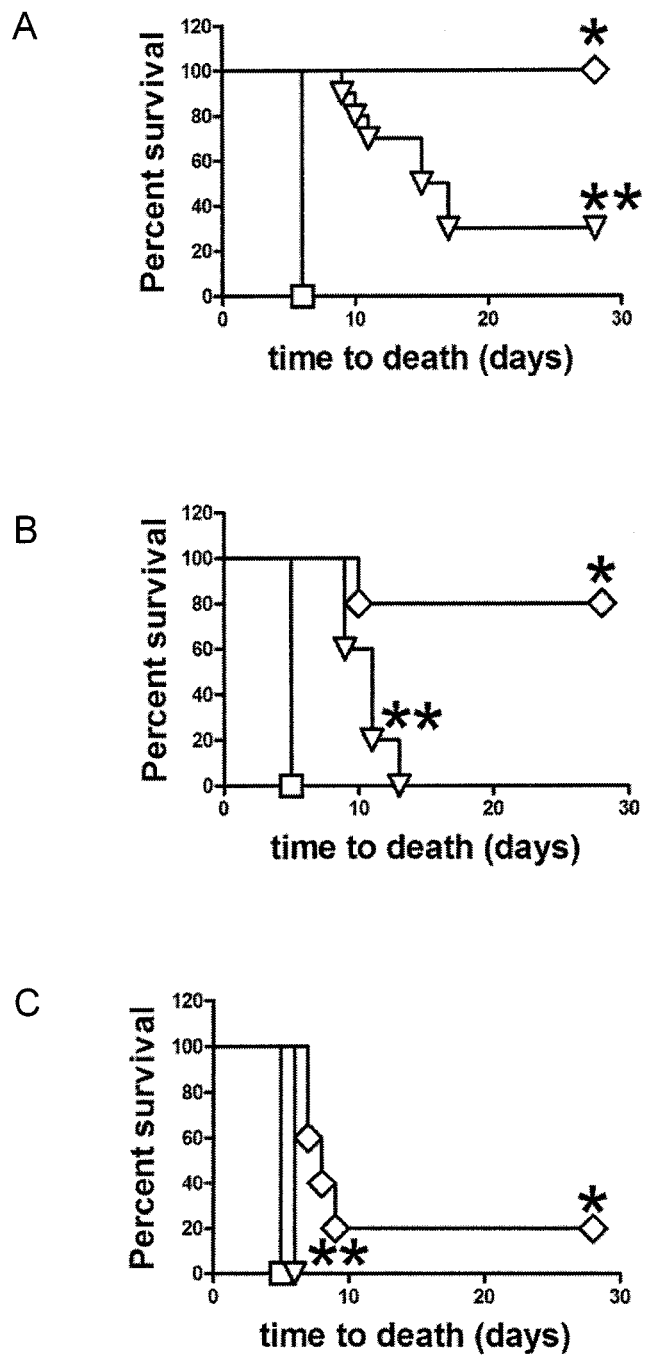
FIG. 4 is a graph showing the survival of BALB/c mice following ID immunization with $10^5$ CFU of LVS (inverted triangle) or SCHU S4ΔclpB (diamond) and subsequent respiratory challenge with 10, 100, or 1000 CFU of SCHU S4 (FIGS. 4A, 4B, and 4C, respectively). *, significantly longer survival than naïve mice or mice immunized with LVS (P<0.05); **, significantly longer survival than naïve mice.

Balb/c mice were immunized ID with $10^5$ CFU of LVS or SCHU S4ΔclpB (of Example 1) then challenged 6 weeks later intranasally with 10, 100, or 1000 CFU of SCHU S4 along with age-matched naïve mice. The results are shown in FIG. 4. It shows that 100% and 80% of mice immunized with SCHU S4ΔclpB survived IN challenge with 10 and 100 CFU of SCHU S4 respectively compared to 30% and 0% of mice immunized with LVS. No immunized mice survived IN challenge with 1000 CFU of SCHU S4, but mice immunized with SCHU S4ΔclpB survived significantly longer than mice immunized with LVS.

EXAMPLE 7

Protection of C57BL/6 Mice

It has been consistently shown that ID vaccination of C57BL/6 mice with LVS fails to protect them against ID or respiratory challenge with SCHU S4.

Figure 5:
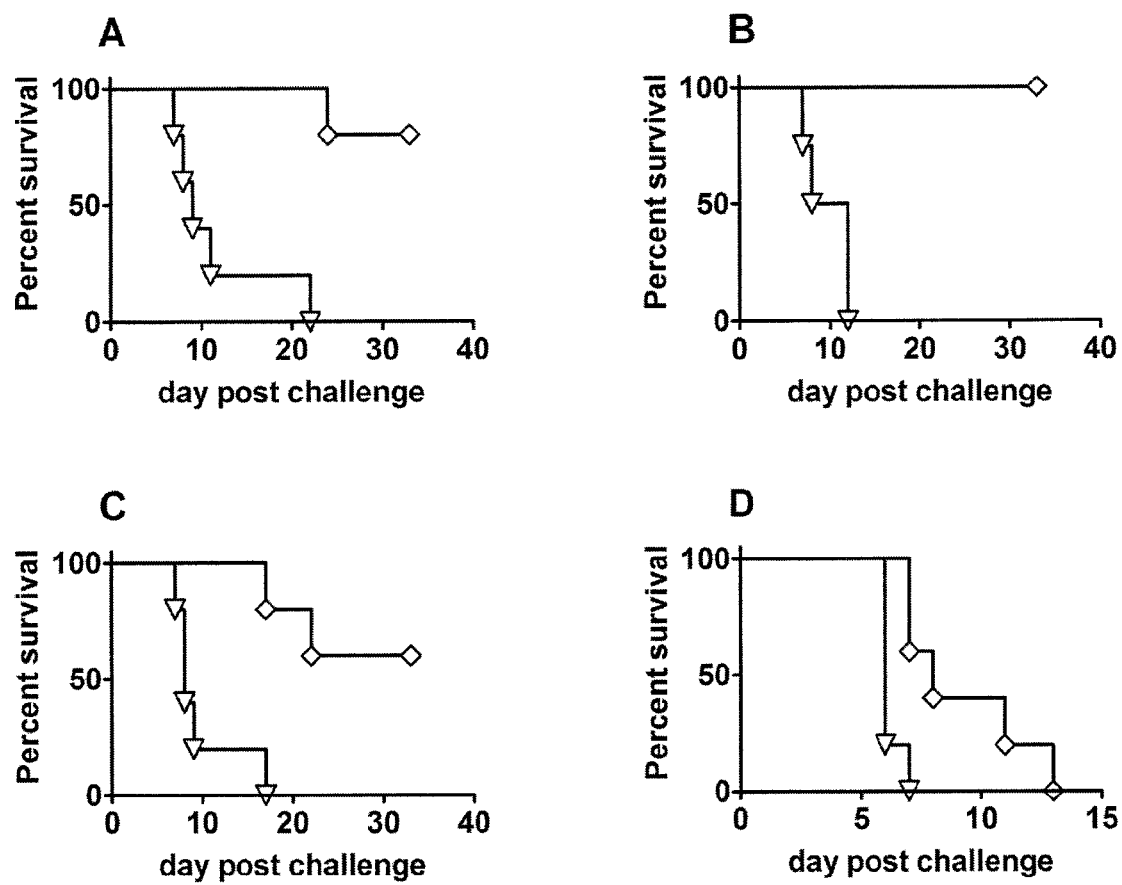
FIG. 5 is a graph showing the survival of C57BL/6 mice following ID immunization with $10^5$ CFU of LVS (inverted triangle) or SCHU S4 ΔclpB (diamond) and subsequent ID challenge with 20 (A), 200 (B), or 2000 (C) CFU of SCHU S4 or IN challenge with 35 CFU (D).
Figure 6:
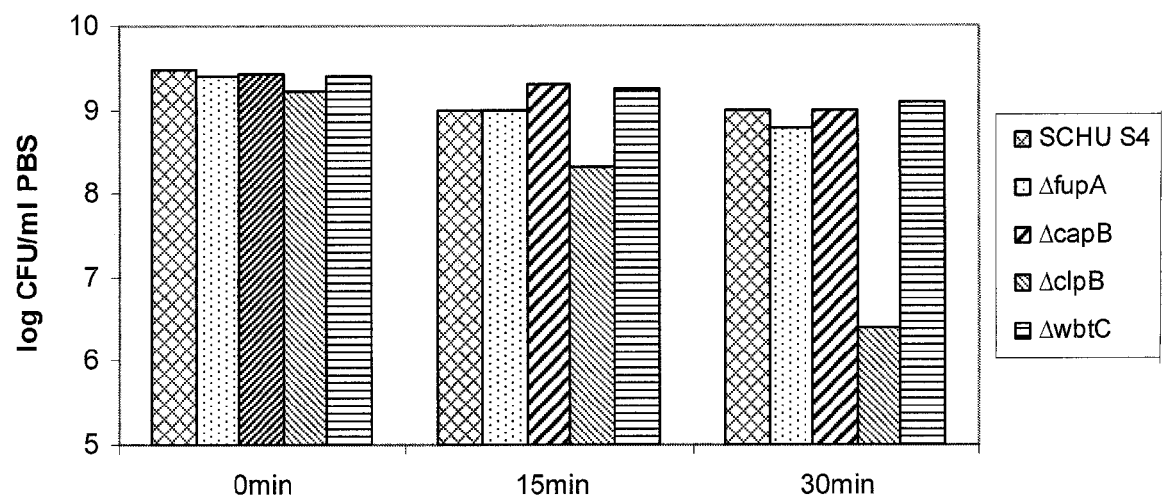
FIG. 6 is a graph comparing the in vitro sensitivity to heat shock of SCHU S4 and various deletion mutants thereof. Wildtype SCHU S4 and various deletion mutants thereof were suspended in saline at a concentration of approximately $10^9$ CFU/ml. Samples were heated to 50° C. and survival was monitored over the course of 30 minutes. Only SCHU S4ΔclpB was unable to withstand this heat stress, losing more than 99% viability within 30 minutes.

C57BL/6 mice were immunized ID with $10^5$ CFU of SCHU S4ΔclpB or LVS, then challenged 6 weeks later with 20, 200, or 2000 CFU of SCHU S4 ID or 20 CFU SCHU S4 IN. The results are shown in FIG. 5. No mice immunized with LVS survived either ID or IN challenge with SCHU S4, whereas 80%, 100%, and 60% of mice immunized with SCHU S4ΔclpB (Example 1) survived ID challenge with 10, 100, or 1000 CFU of SCHU S4. No mice survived IN challenge, but mice immunized with SCHU S4ΔclpB survived longer than mice immunized with LVS. In all cases mice immunized with SCHU S4ΔclpB survived significantly longer (P<0.001) than mice immunized with LVS.

EXAMPLE 8

Resistance to Heat Shock

The degree of sensitivity of the mutant *F. tularensis* strains of Example 1 and other strains to heat treatment was examined.

Wildtype SCHU S4, SCHU S4ΔfupA (SCHU S4 ΔFTT0918; Twine et al, 2005), SCHU S4ΔcapB (Conlan et al, 2010), SCHU S4ΔwbtC, and SCHU S4ΔclpB (Example 1) were individually suspended in saline at a concentration of approximately $10^9$ CFU/ml. Samples were heated to 50° C. and survival was monitored over the course of 30 minutes.

With the exception of SCHU S4ΔclpB, all strains were able to withstand heat stress. However, SCHU S4ΔclpB exhibited a loss of more than 99% viability within 30 minutes. Thus, the clpB gene is clearly required to protect virulent *F. tularensis* from heat stress such as that encountered for a prolonged period in the fevered host.

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

REFERENCES

All patents, patent applications and publications referred to herein are hereby incorporated by reference.

Anthony L S D, Kongshavn P A L. Experimental murine tularemia caused by *Francisella tularensis* live vaccine strain: a model of acquired cellular resistance. Microb Pathog 1987; 2: 3-14.

Chen W, Shen H, Webb A, KuoLee R, Conlan J W. Tularemia in BALB/c and C57BL/6 mice vaccinated with *Francisella tularensis* LVS and challenged intradermally, or by aerosol with virulent isolates of the pathogen; protection varies depending on pathogen virulence, route of exposure, and host genetic background. Vaccine 2003; 21: 3690-700.

Conlan J W, Shen H, Webb A C, Perry M B. Mice vaccinated with the O-antigen of *Francisella tularensis* LVS lipopolysaccharide conjugated to bovine serum albumin develop varying degrees of protective immunity against systemic or aerosol challenge with virulent type A and type B strains of the pathogen. Vaccine 2002; 20: 3465-3471.

Conlan, J. W., Shen, H., KuoLee, R., Zhao, X., Chen, W. Aerosol-, but not intradermal-immunization with the live vaccine strain of *Francisella tularensis* protects mice against subsequent aerosol challenge with a highly virulent type A strain of the pathogen by an áâ T cell- and interferon gamma-dependent mechanism. Vaccine 2005; 23: 2477-85.

Conlan J W, Shen H Golovliov I, Zingmark C, Oyston P C F, Chen W, et al. Differential ability of novel attenuated targeted deletion mutants of *Francisella tularensis* subspecies *tularensis* strain SCHU S4 to protect mice against aerosol challenge with virulent bacteria: effects of host background and route of immunization. Vaccine 2010; 28: 1824-31.

Forslund A-L, Kuoppa K, Svennson K, Salomonsson E, Johansson A, Bystrom M et al. Direct repeat-mediated deletion of a type IV pilin gene results in major virulence attenuation of *Francisella tularensis*. Mol. Microbiol. 2006; 59: 1818-1830.

Fulop M, Mastroeni P, Green M, Titball R W. Role of antibody to lipopolysaccharide in protection against low- and high-virulence strains of *Francisella tularensis*. Vaccine 2001; 19: 4465-72.

Golovliov I, Sjostedt A, Mokrievich A, V. Pavlov V. A method for allelic replacement in *Francisella tularensis*. FEMS Microbiol Lett 2002; 222:273-80.

Green M, Choules G, Rogers D, Titball R W. Efficacy of the live attenuated *Francisella tularensis* vaccine (LVS) in a murine model of disease. Vaccine 2005; 23: 2680-86.

Kadzhaev K, Zingmark C, Golovliov I, Bolanowsi M, Shen H, Conlan W, et al. (2009). Identification of genes contributing to the virulence of *Francisella tularensis* SCHU S4 in a mouse intradermal infection model. PLoS One 2009; 4(5): e5463.

KuoLee R, Harris G, Conlan J W, Chen W. Oral immunization of mice with the live vaccine strain (LVS) of *Francisella tularensis* protects mice against respiratory challenge with virulent type A *F. tularensis*. Vaccine 2007; 25: 3781-91.

Lindgren H, Shen H, Zingmark C, Golovliov I, Conlan W, Sjostedt A. The resistance of *Francisella* strains against reactive nitrogen and oxygen species with special reference to the role of KatG. Infect. Immun 2007; 75: 1303-1309.

Meibom K L. Dubial I, Dupuis M, Barel M, Lenco J, Stulik J et al. The heat-shock protein clpB of *Francisella tularensis* is involved in stress tolerance and is required for multiplication in target organs of infected mice. Mol Microbiol 2008; 67:1384-1401.

Quarry J E, Isherwood K E, Michell S L, Diaper H, Titball R W, Oyston P C F. A *Francisella tularensis* subspecies *novicida* pur F mutant, but not a purA mutant, induces protective immunity to tularemia in mice. Vaccine 2007; 25:2011-2018.

Saslaw S, Eigelsbach H T, Wilson H E, Prior J A, Carhart S. Tularemia vaccine study. I. Intracutaneous challenge. Arch Int Med 1961a; 107: 689-701.

Saslaw S, Eigelsbach H T, Prior J A, Wilson H E, Carhart S. Tularemia vaccine study II. Respiratory challenge. Arch Int Med 1961b; 107: 702-14.

Saslaw S, Carhart S. Studies with tularemia vaccines in volunteers. III. Serologic aspects following intracutaneous or respiratory challenge in both vaccinated and nonvaccinated volunteers. Am J Med Sci 1961; 241: 689-99.

Salomonsson E, Kuoppa K, Forslund A-L, Zingmark, C, Golovliov I, Sjostedt A, et al. (2009). Reintroduction of two deleted virulence loci restores full virulence to the live vaccine strain of *Francisella tularensis*. Infect Immun 2009; 7: 3424-31.

Sebastian S, Dillon S T, Lynch J G, Blalock L-A T, Balon E, Lee K T, et al. A defined O-antigenpolysaccharide mutant of *Francisella tularensis* live vaccine strain has attenuated virulence while retaining its protective capacity. Infect Immun 2007; 75: 2591-2602.

Sjostedt A. Tularemia: History, epidemiology, pathogen physiology and clinical manifestations. Ann New York Acad Sci 2007; 1105: 1-29.

Tempel R, Lai X H, Crosa L, Kozlowicz B, Heffron F. Attenuated *Francisella novicida* transposon mutants protect mice against wild-type challenge. Infect Immun 2006; 74:5095-105.

Thomas R M, Titball R W, Oyston P C F, Griffin K, Waters E, Hitchen P G et al. The Immunologically Distinct O Antigens from *Francisella tularensis* Subspecies *tularensis* and *Francisella novicida* Are both Virulence Determinants and Protective Antigens. Infect Immun 2007; 75:371-378.

Twine S M, Bystrom M, Chen W, Forsman M, Golovliov I R, Johansson A, et al. A mutant of *Francisella tularensis* strain SCHU S4 lacking the ability to express a 58 kDa protein is attenuated for virulence and an effective live vaccine. Infect Immun 2005; 73:8345-52

Twine S M. Petit M, Shen H, Mykytczuk N C S, Kelly J F, Conlan J W. (2006). Immunoproteomic analysis of the murine antibody response to successful and failed immunization with live anti-*Francisella* vaccines. Biochem Biophys Res Commun 2006; 346: 999-1008.

Woolard M D, Hensley L L, Kawula T H, Frelinger J A. et al. (2008). Respiratory *Francisella tularensis* Live Vaccine Strain Infection Induces Th17 Cells and Prostaglandin E2, Which Inhibits Generation of Gamma Interferon-Positive T Cells. Infect. Immun. 2008; 76: 2651-59

Wu T H, Hutt J A, Garrison K A, Berliba L S, Zhou Y, Lyons C R. 2005. Intransal vaccination induces protective immunity against intranasal infection with virulent *Francisella tularensis* biovar A. Infect Immun 2005; 73: 2644-54.

The invention claimed is:

1. An attenuated *Francisella tularensis* mutant strain wherein the caseinolytic peptidase B (c/pB) gene is deleted, wherein the mutant is a variant of the wild-type clinical strain of *F. tularensis* selected from the group consisting of SCHU S4, FS033, FSC 108 and FSC 200.

2. The mutant *F. tularensis* strain of claim 1, wherein the mutant is more attenuated than *F. tularensis* LVS.

3. The mutant *F. tularensis* strain of claim 1, further comprising one or more than one other inactivated genes.

4. The mutant *F. tularensis* strain of claim 3, wherein the one or more than one other inactivated gene is selected from the group consisting of capB, wbtC, ggt, and fupA, or any combination thereof.

5. The mutant *F. tularensis* strain of claim 1, wherein the mutant is CCUG deposit number CCUG 59672.

6. A composition comprising the mutant *F. tularensis* strain of claim 1 and a pharmaceutically acceptable diluent, carrier, or excipient.

7. The composition of claim 6, wherein the composition is a vaccine and the mutant is alive.

8. A method of inducing an immune response against *F. tularensis* in a host comprising administering a mutant *F. tularensis* strain of claim 1 or the composition of claim 6.

9. The method of claim 8, wherein the administration is intradermally (ID), subcutaneously, by scarification, intramuscularly, orally, or by inhalation.

10. The method of claim 8, further comprising a second administration of the mutant *F. tularensis* strain.

* * * * *

UNITED STATES PATENT AND TRADEMARK OFFICE
CERTIFICATE OF CORRECTION

PATENT NO. : 8,993,302 B2  Page 1 of 1
APPLICATION NO. : 13/266466
DATED : March 31, 2015
INVENTOR(S) : Joseph Wayne Conlan and Anders Sjostedt It is certified that error appears in the above-identified patent and that said Letters Patent is hereby corrected as shown below:

Claims

In claim 1, column 19, line 2, "caseinolytic peptidase B (c/pB)" has been corrected to "caseinolytic peptidase B (clpB)"

Signed and Sealed this
Eighth Day of September, 2015

Michelle K. Lee
*Director of the United States Patent and Trademark Office*